United States Patent
Sibenaller et al.

(10) Patent No.: US 9,272,106 B2
(45) Date of Patent: Mar. 1, 2016

(54) RESPIRATION-RATE DEPENDENT RESPIRATORY ASSISTANCE

(75) Inventors: Sara Marie Sibenaller, Pittsburgh, PA (US); Leonardo Alberto Baloa Welzien, Lake Forest, CA (US); Manuel Laura Lapoint, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 436 days.

(21) Appl. No.: 13/995,196

(22) PCT Filed: Dec. 12, 2011

(86) PCT No.: PCT/IB2011/055604
§ 371 (c)(1), (2), (4) Date: Jun. 18, 2013

(87) PCT Pub. No.: WO2012/085748
PCT Pub. Date: Jun. 28, 2012

(65) Prior Publication Data
US 2013/0284174 A1    Oct. 31, 2013

Related U.S. Application Data

(60) Provisional application No. 61/424,839, filed on Dec. 20, 2010.

(51) Int. Cl.
*A61M 11/00* (2006.01)
*A61M 16/00* (2006.01)

(52) U.S. Cl.
CPC ........... *A61M 16/00* (2013.01); *A61M 16/0051* (2013.01); *A61M 2016/003* (2013.01);
(Continued)

(58) Field of Classification Search
CPC ........... A61M 16/00; A61M 16/0003; A61M 16/0009; A61M 16/0051; A61M 2016/0015; A61M 2016/0027; A61M 2016/003; A61M 2016/0036; A61M 2016/0033; A61M 2016/0042; A61M 2205/50; A61M 2230/42
USPC ........................ 128/204.18, 204.21, 204.23
See application file for complete search history.

(56) References Cited

U.S. PATENT DOCUMENTS

5,107,831 A * 4/1992 Halpern et al. .......... 128/204.26
6,119,686 A * 9/2000 Somerson et al. ....... 128/202.22
(Continued)

FOREIGN PATENT DOCUMENTS

EP   0425092 A1   9/1990
EP   2208504 A1   7/2010
(Continued)

OTHER PUBLICATIONS

M.P. Highcock et al; "Functional Differences in Bi-Level Pressure Preset Ventilators", Eur Respir. J., 2001, vol. 17, pp. 268-273.
(Continued)

*Primary Examiner* — Steven Douglas

(57) ABSTRACT

Respiratory assistance is provided to a subject in the form of a pressurized flow of breathable gas. The pressure of the gas is eased during expiration and increased during inspiration. Changes in pressure are triggered and/or cycled based on the monitoring of tidal volume. Volume thresholds that cause triggering and/or cycling are adjusted based on an observed or measured breath rate.

15 Claims, 3 Drawing Sheets

(52) U.S. Cl.
CPC .......... *A61M2016/0027* (2013.01); *A61M 2016/0036* (2013.01); *A61M 2016/0039* (2013.01); *A61M 2205/50* (2013.01); *A61M 2230/42* (2013.01)

(56) References Cited

U.S. PATENT DOCUMENTS

| | | |
|---|---|---|
| 2008/0035147 A1 | 2/2008 | Kirby et al. |
| 2010/0108066 A1 | 5/2010 | Martin et al. |
| 2012/0216811 A1* | 8/2012 | Kimm et al. ............ 128/204.23 |
| 2014/0150796 A1* | 6/2014 | Milne ..................... 128/205.23 |

FOREIGN PATENT DOCUMENTS

| | | |
|---|---|---|
| EP | 2245985 A1 | 11/2010 |
| WO | 2006039587 A1 | 4/2006 |

OTHER PUBLICATIONS

"The Respiratory System and Mechanical Ventilation", Critical Care Education Team RHSCE, 2008, pp. 26-50.

* cited by examiner

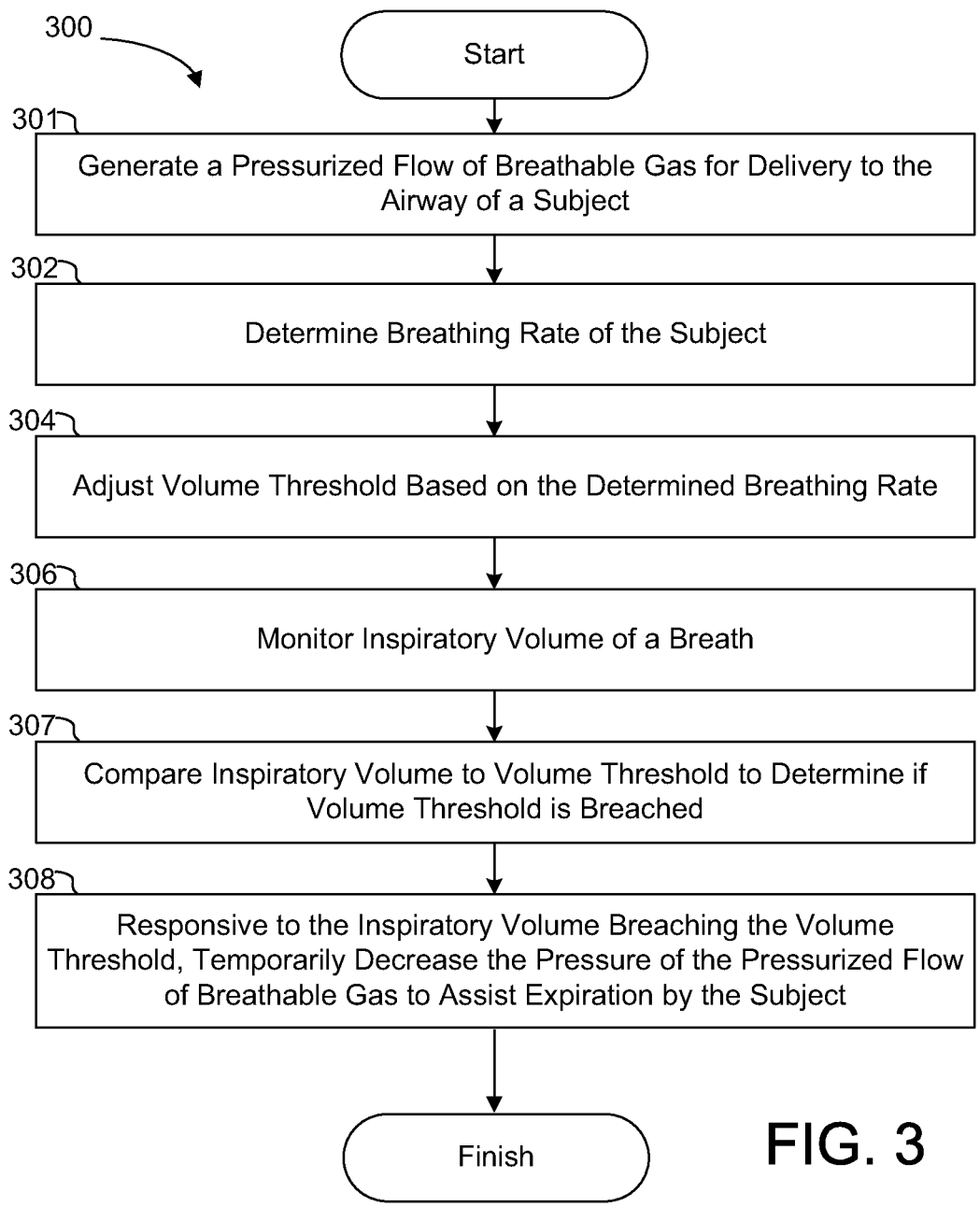

RESPIRATION-RATE DEPENDENT RESPIRATORY ASSISTANCE

BACKGROUND

The invention relates to machine-assisted respiration of a patient.

Machine-assisted respiration of a patient, or subject, is known in the art. Common examples may include positive airway pressure devices, e.g. continuous or bi-level positive airway pressure (CPAP/BiPAP), and/or other devices. A respiratory device may assist a subject to breath in, breath out, or both. A subject may experience discomfort when a respiratory device initiates an inspiration or expiration that fails to coincide with the subject's natural breathing rhythm. Improved comfort may aid improved therapeutic compliance regarding the use of a respiratory device.

The disclosure relates to a method for controlling respiratory assistance of a subject, the subject having an airway. In one embodiment, the method comprises generating a pressurized flow of breathable gas for delivery to the airway of a subject at an inspiratory pressure level during a breath by the subject, wherein the breath has inspiratory volume during an inspiratory phase and expiratory volume during an expiratory phase; determining a breathing rate of the subject; adjusting a first volume threshold based on the determined breathing rate; monitoring the inspiratory volume of the breath by the subject; comparing the inspiratory volume to the first volume threshold to determine when the inspiratory volume of the breath breaches the first volume threshold; and responsive to the inspiratory volume of the breath breaching the first volume threshold, temporarily decreasing the pressure of the pressurized flow of breathable gas from the inspiratory pressure level for expiration by the subject.

Another aspect of the disclosure relates to a system for controlling respiratory assistance of a subject. In one embodiment, the system comprises a pressure generator and one or more processors. The pressure generator is configured to generate a pressurized flow of breathable gas for delivery to the airway of the subject during breaths of the subject, wherein a breath has inspiratory volume during an inspiratory phase and expiratory volume during an expiratory phase. The one or more processors are configured to execute computer program modules including a breathing rate module, an adjustment module, a monitoring module, a comparison module, and a control module. The breathing rate module is configured to determine a breathing rate of the subject. The adjustment module is configured to adjust a first volume threshold based on the determined breathing rate. The monitoring module is configured to monitor inspiratory volumes of individual breaths by the subject. The comparison module is configured to compare the inspiratory volumes of the individual breaths by the subject to the first volume threshold to determine when the inspiratory volumes of the individual breaths have breached the first volume threshold. The control module is configured to control the pressure generator to adjust a pressure level of the pressurized flow of breathable gas, wherein the control module is further configured such that responsive to the inspiratory volume of a given breath breaching the first volume threshold the control module controls the pressure generator to temporarily decrease the pressure level of the pressurized flow of breathable gas for expiration by the subject.

Yet another aspect of the invention relates to a system configured to control volume based respiratory assistance of a subject. In one embodiment, the system comprises means for generating a pressurized flow of breathable gas for delivery to the airway of a subject at an inspiratory pressure level during a breath by the subject, wherein the breath has inspiratory volume during an inspiratory phase and expiratory volume during an expiratory phase; means for determining a breathing rate of the subject; means for adjusting a first volume threshold based on the determined breathing rate; means for monitoring the inspiratory volume of the breath by the subject; means for comparing the inspiratory volume to the first volume threshold to determine when the inspiratory volume of the breath breaches the first volume threshold; and means for temporarily decreasing the pressure level of the pressurized flow of breathable gas from the inspiratory pressure level for expiration by the subject, responsive to the inspiratory volume of the breath breaching the first volume threshold.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment, the structural components illustrated herein are drawn to scale. It is to be expressly understood, however, that the drawings are for the purpose of illustration and description only and are not a limitation. In addition, it should be appreciated that structural features shown or described in any one embodiment herein can be used in other embodiments as well. It is to be expressly understood, however, that the drawings are for the purpose of illustration and description only and are not intended as a definition of limits. As used in the specification and in the claims, the singular form of "a", "an", and "the" include plural referents unless the context clearly dictates otherwise.

BRIEF DESCRIPTION OF THE DRAWING

FIG. 3 illustrates a method of controlling respiratory assistance of a subject.

DETAILED DESCRIPTION OF THE SPECIFIC EMBODIMENTS

Figure 1:
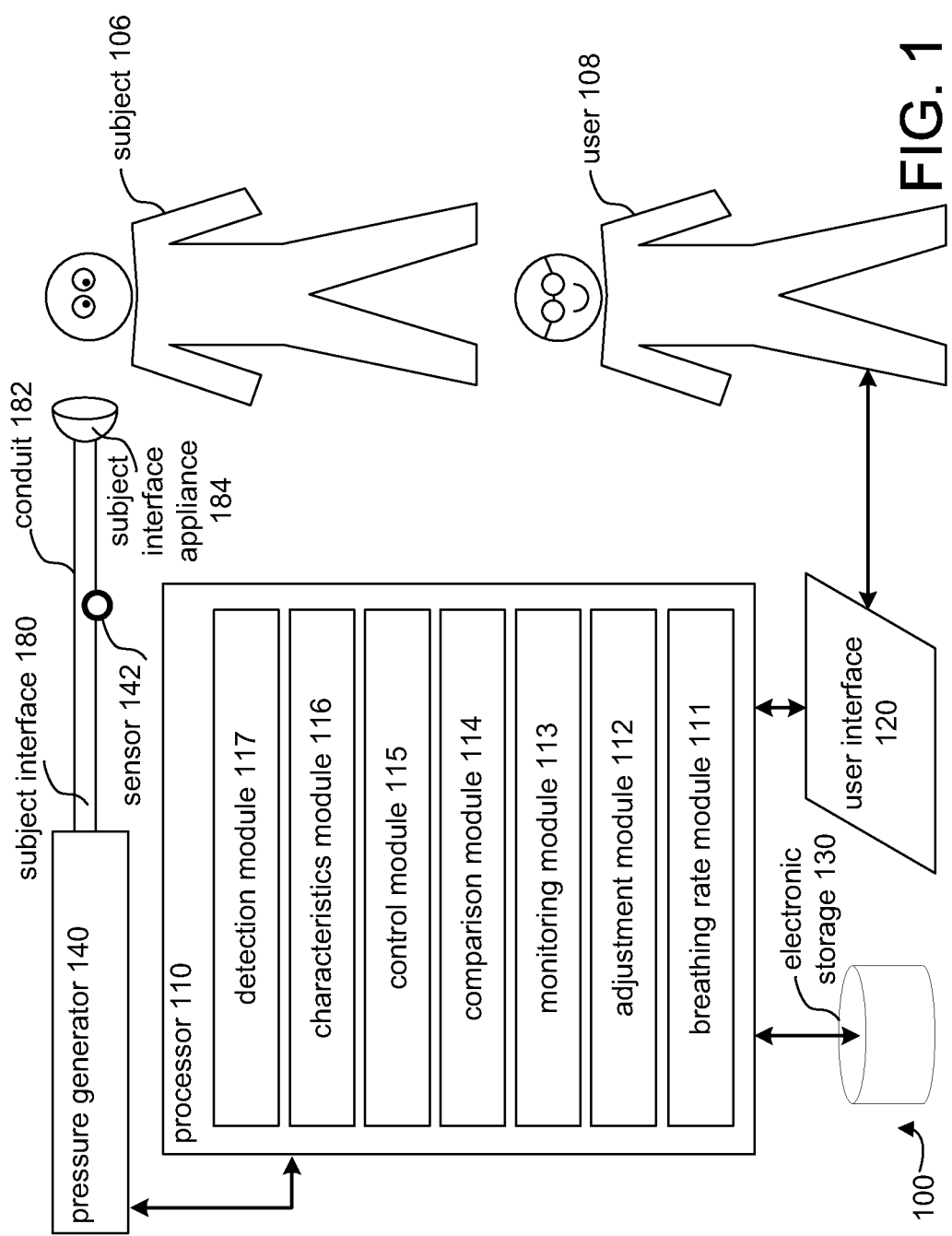
FIG. 1 illustrates a system configured to control respiratory assistance of a subject, a subject, and a user.

FIG. 1 illustrates a system 100 configured to control respiratory assistance of a subject, a subject 106, and a user 108. In particular, system 100 provides respiratory assistance to subject 106 such that the accumulated tidal volume during inspiration and/or expiration may be monitored, and used to control the pressure level of the pressurized flow of breathable gas delivered to the airway of the subject. This may provide more comfortable respiratory assistance for subject 106 than is provided by conventional systems. In one embodiment, system 100 comprises a processor 110, a user interface 120, electronic storage 130, a pressure generator 140, a subject interface 180, one or more sensors 142, and/or other components.

Pressure generator 140 may be configured to provide a pressurized flow of breathable gas for delivery to the airway of the subject. Pressure generator 140 may be configured such that one or more gas parameters of the pressurized flow of breathable gas are controlled in accordance with a therapeutic respiratory regimen for subject 106. The one or more gas parameters may include, for example, one or more of flow, pressure, humidity, velocity, acceleration, and/or other parameters. In one embodiment, pressure generator 140 is a device dedicated to mechanical ventilation. In one embodiment, pressure generator 140 is a positive airway pressure device configured to provide types of therapy other than ventilation, including types of therapy where a subject performs expiration of his own accord or where the device provides negative pressure.

The pressurized flow of breathable gas is delivered from pressure generator 140 to the airway of subject 106 by a subject interface 180. Subject interface 180 may include a conduit 182 and/or a subject interface appliance 184.

Conduit 182 may be a flexible length of hose, or other conduit, that places subject interface appliance 184 in fluid communication with pressure generator 140. Conduit 182 forms a flow path through which the pressurized flow of breathable gas is communicated between subject interface appliance 184 and pressure generator 140.

Subject interface appliance 184 may be configured to deliver the pressurized flow of breathable gas to the airway of subject 106. As such, subject interface appliance 184 may include any appliance suitable for this function. In one embodiment, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject.

Electronic storage 130 may comprise electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a firewire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. Electronic storage 130 may be a separate component within system 100, or electronic storage 130 may be provided integrally with one or more other components of system 100 (e.g., processor 110).

User interface 120 may be configured to provide an interface between system 100 and a user (e.g., user 108, subject 106, a caregiver, a therapy decision-maker, etc.) through which the user may provide information to and receive information from system 100. This enables data, results, and/or instructions and any other communicable items, collectively referred to as "information," to be communicated between the user and system 100. Examples of interface devices suitable for inclusion in user interface 120 include a keypad, buttons, switches, a keyboard, knobs, levers, a display screen, a touch screen, speakers, a microphone, an indicator light, an audible alarm, and a printer.

It is to be understood that other communication techniques, either hard-wired or wireless, are also contemplated by the present invention as user interface 120. For example, in one embodiment, user interface 120 may be integrated with a removable storage interface provided by electronic storage 130. In this example, information may be loaded into system 100 from removable storage (e.g., a smart card, a flash drive, a removable disk, etc.) that enables the user(s) to customize the implementation of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

Sensor 142 may be configured to generate output signals conveying information related to one or more parameters of the pressurized flow of breathable gas. The one or more parameters may include, for example, one or more of a flow, a (tidal) volume, a pressure, a composition (e.g., concentration(s) of one or more constituents), humidity, temperature, acceleration, velocity, acoustics, changes in a parameter indicative of respiration, and/or other parameters. In one embodiment, sensor 142 includes a flow sensor and/or a pressure sensor. Sensor 142 may include one or more sensors that measure such parameters directly (e.g., through fluid communication with the pressurized flow of breathable gas at pressure generator 140 or in subject interface 180). Sensor 142 may include one or more sensors that generate output signals related to one or more parameters of the pressurized flow of breathable gas indirectly. For example, sensor 142 may generate an output based on an operating parameter of pressure generator 140 (e.g., a valve driver or motor current, voltage, rotational velocity, and/or other operating parameters), and/or other sensors.

The illustration of sensor 142 as including a single member in FIG. 1 is not intended to be limiting. In one embodiment sensor 142 includes a plurality of sensors generating output signals as described above. Similarly, the position of sensor 142 in FIG. 1 is not intended to be limiting. Sensor 142 may include one or more sensors located within pressure generator 140 and/or subject interface 180. The output signals generated by sensor 142 may be transmitted to processor 110, user interface 120, and/or electronic storage 130. This transmission may be wired and/or wireless.

Processor 110 is configured to provide information processing capabilities in system 100. As such, processor 110 may include one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 may include a plurality of processing units. These processing units may be physically located within the same device, or processor 110 may represent processing functionality of a plurality of devices operating in coordination.

As is shown in FIG. 1, processor 110 may be configured to execute one or more computer program modules. The one or more computer program modules may include one or more of a breathing rate module 111, an adjustment module 112, a monitoring module 113, a comparison module 114, a control module 115, a characteristics module 116, a detection module 117, and/or other modules. Processor 110 may be configured to execute modules 111, 112, 113, 114, 115, 116, and/or 117 by software; hardware; firmware; some combination of software, hardware, and/or firmware; and/or other mechanisms for configuring processing capabilities on processor 110.

It should be appreciated that although modules 111, 112, 113, 114, 115, 116, and 117 are illustrated in FIG. 1 as being co-located within a single processing unit, in implementations in which processor 110 includes multiple processing units, one or more of modules 111, 112, 113, 114, 115, 116, and/or 117 may be located remotely from the other modules. The description of the functionality provided by the different modules 111, 112, 113, 114, 115, 116, and/or 117 described below is for illustrative purposes, and is not intended to be limiting, as any of modules 111, 112, 113, 114, 115, 116, and/or 117 may provide more or less functionality than is described. For example, one or more of modules 111, 112, 113, 114, 115, 116, and/or 117 may be eliminated, and some or all of its functionality may be provided by other ones of modules 111, 112, 113, 114, 115, 116, and/or 117. As another example, processor 110 may be configured to execute one or more additional modules that may perform some or all of the functionality attributed below to one of modules 111, 112, 113, 114, 115, 116, and/or 117.

Breathing rate module 111 may be configured to determine a breathing rate of the subject. Breathing rate module 111 may use output signals from sensor 142 directly, and/or use information stored in electronic storage 130 that is based on sensor output. As an example, a subject's breathing rate may be determined as a number of inspirations per minute. Breathing rate may also be referred to as breath rate or respiratory rate, and breath rate per minute may be labeled BPM, as shown e.g. in FIG. 2.

Figure 2:
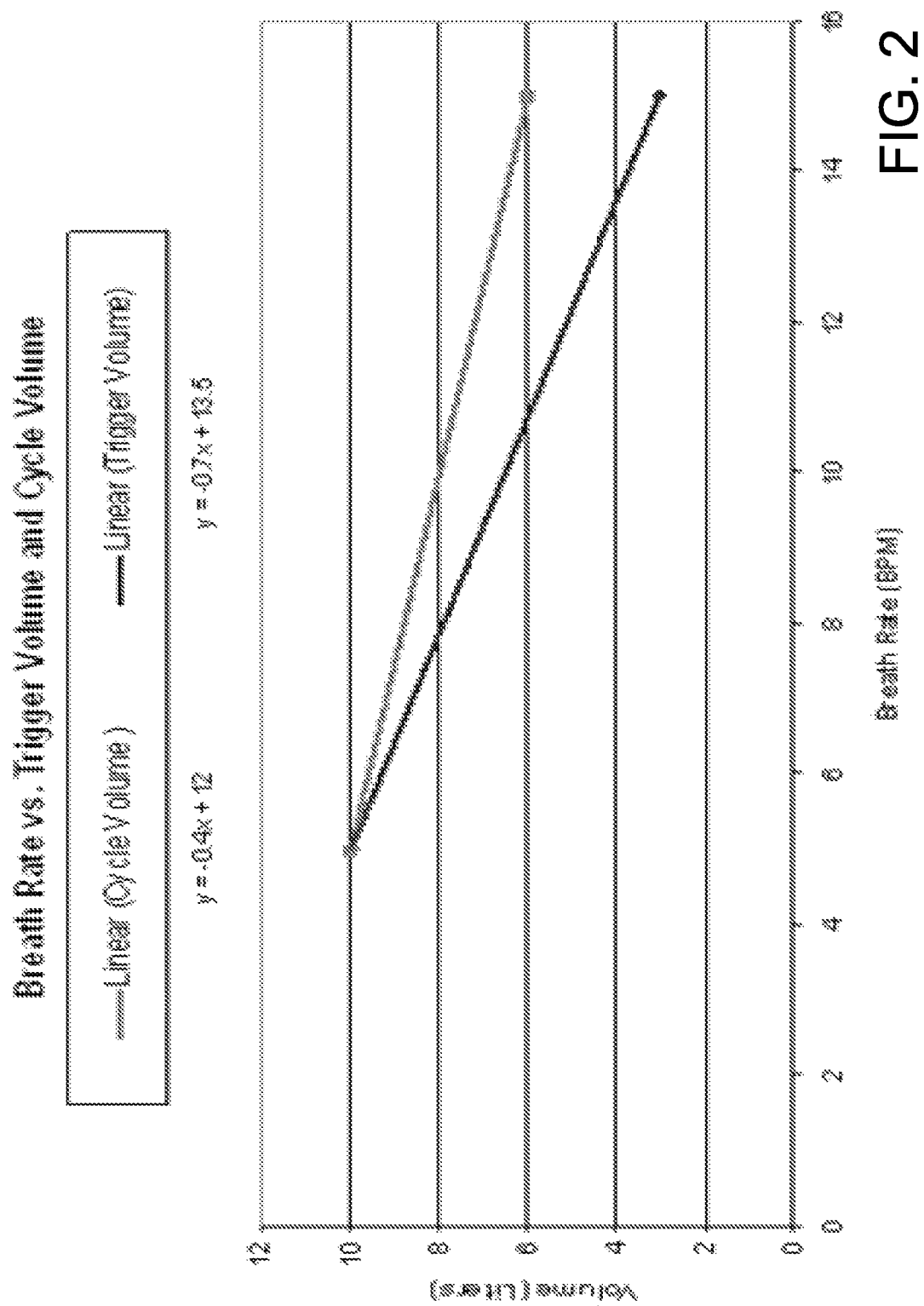
FIG. 2 illustrates two plots of volume thresholds per breathing rate.

Adjustment module 112 may be configured to adjust a (tidal) volume threshold based on the breathing rate. The tidal volume threshold may be increased with a decreasing breathing rate and/or may be decreased with an increasing breathing rate to reflect the impact of breathing rate on tidal volume. By way of non-limiting example, assume a subject is using a BiPAP device for respiratory assistance. The expiratory tidal volume threshold may be set at a predetermined volume, such that breaching this threshold causes a BiPAP device to initiate assistance for the subsequent inspiration by the subject. Initiating this assistance may be referred to as "cycling." Consequently, the expiratory tidal volume may be referred to as "cycle volume," as shown in FIG. 2. The inspiratory tidal volume threshold may be set at a predetermined volume, such that breaching this threshold causes a BiPAP device to initiate assistance for the subsequent expiration by the subject. Initiating this assistance may be referred to as "triggering." Consequently, the inspiratory tidal volume may be referred to as "trigger volume," as shown in FIG. 2. Adjustment module 112 takes into account the inverse relationship between breathing rate and tidal volume during natural smooth breathing. Simply put, if a subject takes fewer breaths per minute, each breath taken typically has a greater tidal volume compared to an instance when the subject takes more breaths per minute. As the tidal volume naturally varies based on breathing rate, so may a tidal volume threshold vary, be it inspiratory or expiratory. The adjustment of a tidal volume threshold based on the breathing rate may be performed based on an equation that represents an inverse relationship between breathing rate and tidal volume for common breathing rates. Alternatively, and/or simultaneously, the adjustment may be performed based on the functionality of a look-up table.

By way of illustration, FIG. 2 illustrates two plots of volume thresholds per breathing rate, as may be used by adjustment module 112. FIG. 2 shows one plot for an expiratory tidal volume threshold (labeled "Cycle Volume") per BPM, and one plot for an inspiratory tidal volume threshold (labeled "Trigger Volume") per BPM. The range of plotted breathing rates extends to common breathing rates, i.e. from 5 BPM to 15 BPM. The plotted relationships in FIG. 2 are linear and thus defined by any two points. Using more points per plot is within the scope of the present technology. Using logarithmic, polynomial, exponential, and/or moving average manipulation of two or more points to derive a relationship for adjusting a volume threshold per breathing rate is envisioned. For example, in FIG. 2, the expiratory tidal volume threshold for a breathing rate of fifteen breaths per minute is about six liters. Similarly, in FIG. 2, the inspiratory tidal volume threshold for a breathing rate of eight breaths per minute is about eight liters. The determination of a tidal volume threshold for a given breathing rate may also be accomplished by using a look-up table.

Monitoring module 113 may be configured to monitor inspiratory and/or expiratory volume of individual breaths by a subject. Monitoring module 113 may use output signals from sensor 142 directly, and/or use information stored in electronic storage 130 that is based on sensor output.

Comparison module 114 may be configured to compare the inspiratory volume of an individual breath by the subject to an inspiratory volume threshold to determine when the inspiratory volume of the individual breath has breached the inspiratory volume threshold. Alternatively, and/or additionally, comparison module 114 may be configured to compare the expiratory volume of an individual breath by the subject to an expiratory volume threshold to determine when the expiratory volume of the individual breath has breached the expiratory volume threshold. Comparison module 114 may use different volume thresholds for inspiration and expiration. In conjunction with adjustment module 112, these volume thresholds may vary based on breathing rate. In one embodiment, adjustment module 112 adjusts the inspiratory and/or the expiratory volume thresholds based on breathing rate in the manner described above.

Control module 115 may be configured to control pressure generator 140 to adjust the parameters of the pressurized flow of breathable gas in accordance with a therapy regimen. In one embodiment, the therapy regimen dictates that control module 115 controls pressure generator 140 such that the pressurized flow of breathable gas is delivered to the airway of subject 106 at a first pressure level during inspiration. The first pressure level is sufficiently high that the lungs of subject 106 are at least partially filled during inspiration. At some moment, e.g. indicated by comparison module 114, control module 115 controls pressure generator 140 to reduce the pressure of the pressurized flow of breathable gas to assist expiration by the subject. After expiration is complete, control module 115 then controls pressure generator 140 to return the pressure of the pressurized flow of breathable gas to the first pressure level to facilitate another inspiration. A subject may experience discomfort when a respiratory device initiates an inspiration or expiration that fails to coincide with the subject's natural breathing rhythm. Improved comfort may aid improved therapeutic compliance regarding the use of a respiratory device. Improved synchronization of a subject's breathing rhythm may also lead to improved accuracy for determining breathing parameters such as breathing rate, duration of inspiration or expiration, and derived parameters such as respiratory events that are based on inspiratory characteristics and/or expiratory characteristics.

Characteristics module 116 may be configured to determine inspiration characteristics and expiration characteristics, which may include begin time, duration, and end time of either an individual inspiration or expiration, or the average duration of a set of inspirations or expirations spanning a specific duration of time. The specific duration of time may be a minute, an hour, a day, a week, a month, or a user-configurable duration of time. Additional characteristics may include inspiration rates, expiration rates, and variability of the individual or average duration of inspiration or expiration.

Detection module 117 may be configured to detect respiratory events, e.g. apneas or hypopneas, based on the inspiration characteristics and expiration characteristics determined by characteristics module 116. A respiratory event could be characterized by the ratio of the duration of an inspiration and the duration of an expiration.

FIG. 3 illustrates a method 300 of controlling respiratory assistance of a subject. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 301, a pressurized flow of breathable gas for delivery to the airway of a subject is generated. In one embodiment, operation 301 is performed by a pressure generator similar to or substantially the same as pressure generator 140 (shown in FIG. 1 and described above) under control of a control module similar to or substantially the same as control module 115 (shown in FIG. 1 and described above).

At an operation 302, a breathing rate of the subject is determined. In one embodiment, operation 302 is performed by a breathing rate module similar to or substantially the same as breathing rate module 111 (shown in FIG. 1 and described above).

At an operation 304, a volume threshold is adjusted based on the determined breathing rate. In one embodiment, operation 304 is performed by an adjustment module similar to or substantially the same as adjustment module 112 (shown in FIG. 1 and described above).

At an operation 306, the inspiratory volume of a breath by the subject is monitored. In one embodiment, operation 306 is performed by a monitoring module similar to or substantially the same as monitoring module 113 (shown in FIG. 1 and described above).

At an operation 307, the inspiratory volume is compared to the volume threshold to determine if the inspiratory volume breaches the volume threshold. In one embodiment, operation 307 is performed by a comparison module similar to or substantially the same as comparison module 114 (shown in FIG. 1 and described above).

At an operation 308, responsive to the inspiratory volume breaching the volume threshold, the pressure of the pressurized flow of breathable gas is temporarily decreased to assist expiration by the subject. In one embodiment, operation 307 is performed by a control module similar to or substantially the same as control module 115 (shown in FIG. 1 and described above).

Details included herein are for the purpose of illustration based on what is currently considered to be the most practical and preferred embodiments, it is to be understood that such detail is solely for that purpose and that the scope of this specification is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A method for controlling respiratory assistance of a subject, the subject having an airway, the method comprising:
generating a pressurized flow of breathable gas for delivery to the airway of a subject at an inspiratory pressure level during a breath by the subject, wherein the breath has inspiratory volume during an inspiratory phase and expiratory volume during an expiratory phase;
determining a breathing rate of the subject;
adjusting a first volume threshold based on the determined breathing rate;
monitoring the inspiratory volume of the breath by the subject;
comparing the inspiratory volume to the first volume threshold to determine when the inspiratory volume of the breath breaches the first volume threshold; and
responsive to the inspiratory volume of the breath breaching the first volume threshold, temporarily decreasing the pressure of the pressurized flow of breathable gas from the inspiratory pressure level for expiration by the subject.

2. The method of claim 1, further comprising:
adjusting a second volume threshold based on the determined breathing rate;
monitoring the expiratory volume of the breath;
comparing the expiratory volume of the breath to the second volume threshold to determine when the expiratory volume of the breath breaches the second volume threshold; and
responsive to the expiratory volume of the breath breaching the second volume threshold, returning the pressure level of the pressurized flow of breathable gas to the inspiratory pressure level.

3. The method of claim 2, further comprising:
determining inspiration characteristics and expiration characteristics; and
detecting respiratory events based on the inspiration characteristics and expiration characteristics.

4. The method of claim 1, wherein adjustment of the first volume threshold is performed based on an equation that represents an inverse relationship between breathing rate and tidal volume for common breathing rates.

5. The method of claim 2, wherein the first volume threshold is not higher than the second volume threshold for common breathing rates.

6. A system for controlling respiratory assistance of a subject, the subject having an airway, the system comprising:
a pressure generator configured to generate a pressurized flow of breathable gas for delivery to the airway of the subject during breaths of the subject, wherein a breath has inspiratory volume during an inspiratory phase and expiratory volume during an expiratory phase; and one or more processors configured to execute computer program modules, the computer program modules comprising:

a breathing rate module configured to determine a breathing rate of the subject, an adjustment module configured to adjust a first volume threshold based on the determined breathing rate, a monitoring module configured to monitor inspiratory volumes of individual breaths by the subject, a comparison module configured to compare the inspiratory volumes of the individual breaths by the subject to the first volume threshold to determine when the inspiratory volumes of the individual breaths have breached the first volume threshold, and a control module configured to control the pressure generator to adjust a pressure level of the pressurized flow of breathable gas, wherein the control module is further configured such that responsive to the inspiratory volume of a given breath breaching the first volume threshold the control module controls the pressure generator to temporarily decrease the pressure level of the pressurized flow of breathable gas for expiration by the subject.

7. The system of claim 6, wherein the adjustment module is further configured to adjust a second volume threshold based on the determined breathing rate, wherein the monitoring module is further configured to monitor expiratory volumes of individual breaths by the subject, wherein the comparison module is further configured to compare the expiratory volumes of the individual breaths by the subject to the second volume threshold to determine when the expiratory volumes of the individual breaths have breached the second volume threshold, and wherein the control module is further configured such that responsive to the expiratory volume of a given breath breaching the second volume threshold the control module controls the pressure generator to temporarily increase the pressure level of the pressurized flow of breathable gas for inspiration by the subject.

8. The system of claim 7, further comprising:

a characteristics module configured to determine inspiration characteristics and expiration characteristics; and a detection module configured to detect respiratory events based on the inspiration characteristics and the expiration characteristics.

9. The system of claim 6, wherein the adjustment module is configured such that adjustment of the first volume threshold is performed based on an equation that represents the inverse relationship between breathing rate and tidal volume for common breathing rates.

10. The system of claim 6, further comprising a subject interface configured to deliver the pressurized flow of breathable gas to the airway of the subject, wherein the subject interface includes a conduit and a subject interface appliance, and wherein the conduit is configured to provide fluid communication between the subject interface appliance and the pressure generator.

11. A system configured to control volume based respiratory assistance of a subject, the subject having an airway, the system comprising:

means for generating a pressurized flow of breathable gas for delivery to the airway of a subject at an inspiratory pressure level during a breath by the subject, wherein the breath has inspiratory volume during an inspiratory phase and expiratory volume during an expiratory phase;

means for determining a breathing rate of the subject;

means for adjusting a first volume threshold based on the determined breathing rate;

means for monitoring the inspiratory volume of the breath by the subject;

means for comparing the inspiratory volume to the first volume threshold to determine when the inspiratory volume of the breath breaches the first volume threshold; and means for temporarily decreasing the pressure level of the pressurized flow of breathable gas from the inspiratory pressure level for expiration by the subject, responsive to the inspiratory volume of the breath breaching the first volume threshold.

12. The system of claim 11, wherein the means for adjusting a first volume threshold based on the determined breathing rate is further configured for adjusting a second volume threshold based on the determined breathing rate, wherein the means for monitoring the inspiratory volume of the breath by the subject is further configured for monitoring the expiratory volume of the breath by the subject, wherein the means for comparing the inspiratory volume of the breath by the subject to the first volume threshold is further configured for comparing the expiratory volume of the breath by the subject to the second volume threshold to determine when the expiratory volume of the breath breaches the second volume threshold, and wherein the means for temporarily decreasing the pressure level of the pressurized flow of breathable gas is further configured for returning the pressure level of the pressurized flow of breathable gas to the inspiratory level, responsive to the expiratory volume of the breath breaching the second volume threshold.

13. The system of claim 12, further comprising:

means for determining inspiration characteristics and expiration characteristics; and means for detecting respiratory events based on the inspiration characteristics and expiration characteristics.

14. The system of claim 11, wherein the operation of the means for adjusting a first volume threshold based on the determined breathing rate includes is performed based on an equation that represents an inverse relationship between breathing rate and tidal volume for common breathing rates.

15. The system of claim 12, wherein the first volume threshold is not higher than the second volume threshold for common breathing rates.

* * * * *